US006989130B2

(12) United States Patent
Deshmukh

(10) Patent No.: US 6,989,130 B2
(45) Date of Patent: Jan. 24, 2006

(54) METHOD AND AUTOMATED FLUIDIC SYSTEM FOR DETECTING PROTEIN IN BIOLOGICAL SAMPLE

(75) Inventor: A Jay Deshmukh, Gyeonggi-do (KR)

(73) Assignee: Samsung Electronics Co., Ltd., (KR)

( * ) Notice: Subject to any disclaimer, the term of this patent is extended or adjusted under 35 U.S.C. 154(b) by 0 days.

(21) Appl. No.: 10/761,846

(22) Filed: Jan. 20, 2004

(65) Prior Publication Data

US 2004/0152200 A1 Aug. 5, 2004

(30) Foreign Application Priority Data

Feb. 20, 2003 (KR) ...................... 10-2003-0003668

(51) Int. Cl.
*G01N 21/00* (2006.01)
*G01N 31/00* (2006.01)
*G01N 33/00* (2006.01)

(52) U.S. Cl. ............................ 422/81; 422/57; 422/63; 422/68.1; 422/103; 422/104; 435/287.1; 435/287.2; 435/287.9; 435/288.4; 435/288.5; 436/518

(58) Field of Classification Search .................. 422/63, 422/81, 103–104, 50, 57, 68.1, 99–100; 435/7.1, 435/287.2, 287.9, 288.4, 288.5, 4; 436/43, 436/54, 174, 180
See application file for complete search history.

(56) References Cited

U.S. PATENT DOCUMENTS

| | | | | | |
|---|---|---|---|---|---|
| 4,381,099 | A | * | 4/1983 | Knedlik | 251/14 |
| 4,598,628 | A | * | 7/1986 | Courtright | 91/481 |
| 4,895,706 | A | * | 1/1990 | Root et al. | 422/102 |
| 5,219,529 | A | * | 6/1993 | Ngo et al. | 422/101 |
| 5,321,123 | A | * | 6/1994 | Griffin et al. | 530/300 |
| 5,601,991 | A | * | 2/1997 | Oberhardt | 435/7.91 |
| 5,697,132 | A | * | 12/1997 | DeCarbo et al. | 27/22.1 |
| 5,834,222 | A | * | 11/1998 | Friedman et al. | 435/7.93 |
| 6,033,911 | A | | 3/2000 | Schultz et al. | 436/49 |
| 6,083,763 | A | * | 7/2000 | Balch | 436/518 |
| 6,093,869 | A | * | 7/2000 | Roe et al. | 604/361 |
| 6,117,396 | A | * | 9/2000 | Demers | 422/100 |
| 6,146,595 | A | * | 11/2000 | Mikulsky | 422/101 |
| 6,395,232 | B1 | * | 5/2002 | McBride | 422/100 |
| 6,479,301 | B1 | | 11/2002 | Balch et al. | 436/518 |
| 6,485,690 | B1 | * | 11/2002 | Pfost et al. | 422/102 |
| 6,729,352 | B2 | * | 5/2004 | O'Connor et al. | 137/827 |
| 2003/0069411 | A1 | * | 4/2003 | Brennan | 536/25.3 |

FOREIGN PATENT DOCUMENTS

| | | |
|---|---|---|
| KR | 2002-0043553 | 6/2002 |
| KR | 2002-0071853 | 9/2002 |
| WO | WO 00/78456 A1 | 12/2000 |
| WO | WO 01/62377 A2 | 8/2001 |

* cited by examiner

*Primary Examiner*—Long V. Le
*Assistant Examiner*—Leon Y. Lum
(74) *Attorney, Agent, or Firm*—Cantor Colburn LLP

(57) ABSTRACT

An automated microfluidic system that includes a cartridge reservoir part, a cartridge, a compressed-air storage tank, a buffer storage tank, and a reader is provided. The automated microfluidic system that detects a particular protein in a biological sample by enzyme-linked immunosorbent assay (ELISA) can automate a series of assaying processes, beginning with sample injection and ending with detection, with a simple structure, thereby allowing for convenient and quick detection of a particular protein in a biological sample without requiring skillful, elaborate manipulations by an operator.

12 Claims, 2 Drawing Sheets

METHOD AND AUTOMATED FLUIDIC SYSTEM FOR DETECTING PROTEIN IN BIOLOGICAL SAMPLE

BACKGROUND OF THE INVENTION

This application claims the priority of Korean Patent Application No. 2003-3668, filed on Jan. 20, 2003, in the Korean Intellectual Property Office, the disclosure of which is incorporated herein in its entirety by reference.

1. Field of the Invention

The present invention relates to a biomolecular detection apparatus, and more particularly, to an automated fluidic system for detecting protein in a biological sample.

2. Description of the Related Art

Most diagnostic methods involve a main step of detecting whether a particular protein exists in a biological sample. Various diagnostic methods, such as enzyme-linked immunosorbent assay (ELISA), radioimmunoassay (RIA), fluorometry, nuclear magnetic resonance spectroscopy, and calorimetric assay, have been widely used, with the ELISA method being the most common.

There are three technologies involved in detecting a particular protein by ELISA: an antigen-antibody chemical reaction technology, in which an antibody that can be immobilized on a substrate or can be labeled with an enzyme is reacted with a protein of interest; an optical detection technique, in which a color variation in the substrate caused by the reaction with the enzyme is optically measured; and a fluid handling technology, in which various fluids are supplied to a multi-well plate in a predetermined order and the multi-well plate is washed between the steps of supplying the various fluids.

The fluid handling technology requires elaborate manipulations by a skilled operator for each step, for example, pipetting fluid into the multi-well plate and flushing the fluid, and takes much time. Therefore, an automated fluid manipulation process to allow for easier protein detection and to reduce the time required for detection is required.

To meet this requirement, various automated systems for manipulating and assaying components in each reservoir when detecting protein using a multi-well plate have been developed.

Korean Laid-open Patent Publication No. 2003-435543 discloses a micro-fluidic control system that includes a series of channels that allow a very small fraction of fluid to pass.

Korean Laid-open Patent Publication No. 2002-71853 discloses a system and method for detecting and identifying various molecular events in a test sample. The system includes fluid storage reservoirs, a signal supply unit that transmits an input test signal, a detecting probe, and a signal detection unit.

U.S. Pat. No. 6,033,911 discloses an automated assaying device that includes a plurality of controllable lumens arranged to form clusters, which are separately controlled according to sample inflow and outflow. This automated assaying device includes a unique washing system capable of washing the entire assaying system.

However, a series of assaying processes, including sample injection, channel washing, dye injection, channel washing, and sample detection, cannot be fully automated with the above-described conventional automated assay devices. In addition, the conventional automated assay systems require a separate power source and a skilled operator due to their structural complexity, for maintenance and repair as well as operation. Further, the conventional automated assay systems are expensive and uneconomical.

SUMMARY OF THE INVENTION

The present invention provides an automated fluidic system that detects a particular protein in a biological sample by enzyme-linked immonosorbent assay (ELISA), in which a series of assay processes, beginning with sample injection and ending with detection, is automated with a simple structure, thereby allowing for convenient and quick detection of a particular protein in a biological sample without requiring skillful, elaborate manipulations by an operator.

In one aspect of the present invention, there is provided an automated microfluidic system that detects a protein in a biological sample, the system including: a cartridge reservoir part including a sample reservoir, a dye reservoir, and a plurality of control reservoirs that contain control solutions of various concentrations of the protein of interest , each of the sample reservoir, the dye reservoir, and the control reservoirs having a hydrophobic upper barrier connected to a compressed-air inlet and a hydrophobic lower barrier connected to a liquid outlet; a cartridge with a microfluidic channel that includes a sample detection part, a plurality of control detection parts, and a dye/buffer inlet part, each of the sample detection part and the control detection parts that have inlets connected to the liquid outlets of the sample reservoir and control reservoirs, respectively, an outlet, and antibodies immobilized on an inner surface, the dye/buffer inlet part having a dye inlet connected to a liquid outlet of the dye reservoir and a buffer inlet port; a compressed-air storage tank connected to the compressed-air inlets of the sample reservoir, the dye reservoirs, and the control reservoirs by valves; a buffer storage tank connected to the buffer inlet ports by valves; and a reader that measures the degrees of antigen-antibody reactions in the sample and control detection parts based on variations in dye color.

The present invention also provides a method of detecting a protein in a biological sample using the above automated microfluidic system, the method comprising: supplying compressed air through the compressed-air inlets to move a sample in the sample reservoir and controls in the control reservoirs into the sample detection part and the control detection parts, respectively, to induce antigen-antibody reactions therein; washing the sample detection part and the control detection parts by supplying a buffer through the buffer inlet port; supplying compressed air through the compressed-air inlets to move a dye in the dye reservoir through the dye/buffer inlet port into the sample detection part and the control detection parts; washing the sample detection part and the control detection parts by supplying a buffer through the buffer inlet port; and detecting whether the protein exists in the biological sample and quantitating the protein based on color variation data obtained from the antigen-antibody reactions in the sample detection part and the control detection parts.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
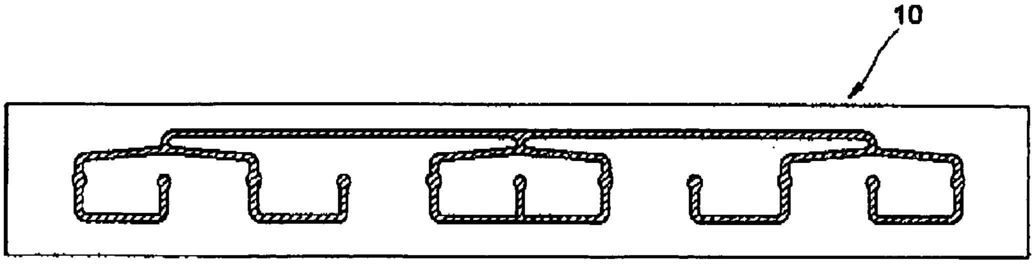
FIG. 1 is an illustration of a microfluidic channel according to the present invention.

An automated fluidic system according to an embodiment of the present invention includes a disposable cartridge, a compressed air storage tank, a buffer storage tank, and a detection unit.

The cartridge of the automated fluidic system according to the present invention includes a sample reservoir, control reservoirs, and a dye reservoir. Hereinafter, the sample reservoir, the control reservoir, and the dye reservoir will be collectively referred to as a cartridge reservoir part 9.

The sample reservoir contains a biological sample that contains a target protein of interest. Any biological sample, for example, blood, urine, cerebrospinal fluid, saliva, tissue fluid, which contains a target protein that can be detected by enzyme-linked immunosorbent assay (ELISA), may be used.

The control reservoirs contain a control solution of a known concentration of a target protein to be detected. The concentration of the target protein in the biological sample can be calculated using a calibration curve of the control solution.

The dye reservoir contains a dye that can specifically bind to the target protein and label an antibody 13 (see FIG. 2) attached to the internal surface of a microfluidic channel 10, which will be described later. Any dye that can produce an optically detectable signal in response to the reaction of the antigen (target protein) and the antibody 13 attached to the interior surface of the microfluidic channel 10 may be used without limitations. Examples of such a dye that may be used in the present invention include a fluorescent dye, a chemiluminescent dye, a phosphorescent dye, and the like.

The cartridge, which includes the cartridge reservoir part 9, may be made of an acryl resin, a polyethylene resin, a polypropylene resin, etc. The cartridge may have a width of 5–10 cm, a length of 2–5 cm, and a height of 2–5 cm. Each of the sample reservoir, the control reservoirs, and the dye reservoir may have a capacity of 100–500 $\mu$L of liquid.

The cartridge reservoir part 9 includes one sample reservoir, one or two dye reservoirs, and two or three control reservoirs.

Each of the reservoirs in the cartridge reservoir part 9 has a hydrophobic upper barrier 7 connected to a compressed-air inlet 6 and a hydrophobic lower barrier 8 connected to a liquid outlet. These hydrophobic barriers 7 and 8, which are porous, may be manufactured to allow only air to pass, not liquid, in an atmospheric pressure. The lower hydrophobic barrier 8 may have a larger average pore size than the upper hydrophobic barrier 7.

The upper and lower hydrophobic barriers 7 and 8 are made of polytetrafluoro ethylene membranes. The upper hydrophobic barrier 7 has pores of a diameter that ranges from 0.2 $\mu$m to 1 $\mu$m. The lower hydrophobic barrier 8 has pores of a diameter that ranges from 2 $\mu$m to 20 $\mu$m. The upper hydrophobic barrier 7 allows a predetermined liquid to pass only when a higher pressure is applied than to the lower hydrophobic barrier 8. For example, when the upper hydrophobic barrier 7 has a pore diameter of 0.45 $\mu$m and the lower hydrophobic barrier 8 has a pore diameter of 10 $\mu$m, the former can pass water at a pressure of 2 atm whereas the later can pass water at a pressure of 0.1 atm. The gaps between the upper and lower hydrophobic barriers and each of the reservoirs in the cartridge reservoir part 9 may be sealed using, for example, O-rings.

The upper and lower ends of each of the reservoirs in the cartridge reservoir part 9 are blocked by the upper and lower hydrophobic barriers 7 and 8 that have different pore sizes, so that liquid in each of the reservoirs can be discharged only through the lower hydrophobic barrier 8, not the upper hydrophobic barrier 7, when a predetermined pressure is applied via a corresponding compressed-air inlet 6.

The liquid discharged through the lower hydrophobic barrier 8 flows toward a microfluidic channel 10. The microfluidic channel 10 has a structure as illustrated in FIG. 1, which is a plan view of the microfluidic channel 10.

Figure 2:
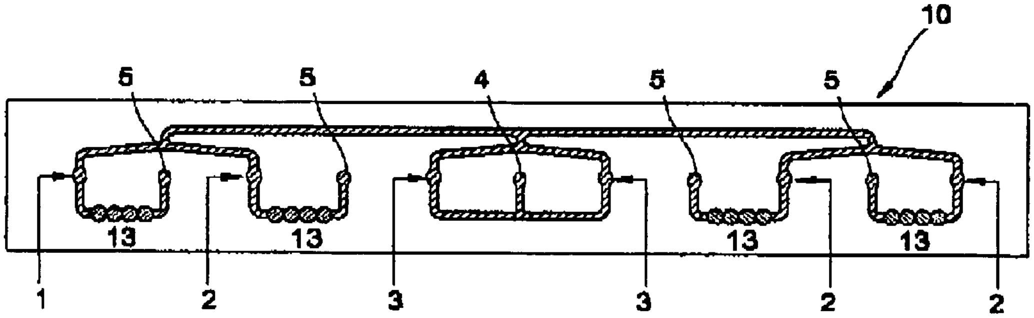
FIG. 2 is an illustration of a microfluidic channel showing inlets for a sample, a control, a dye and a buffer solution, and antibodies attached to an internal surface of the micro-fluidic channel.

In an automated microfluidic system shown in FIG. 2, which includes one sample reservoir, two dye reservoirs, and three control reservoirs, the microfluidic channel 10 includes one sample detection part, three control detection parts, and two dye/buffer inlet parts. Each of the sample and control detection parts has a sample inlet 1 or a control inlet 2, which are connected to the liquid outlets of the sample and control reservoirs, respectively, and an outlet 5, and includes antibodies 13 immobilized on an inner surface. The dye/buffer inlet parts have two dye inlets 3 connected to liquid outlets of the dye reservoir and a buffer inlet port 4.

The antibodies 13 that specifically bind to a target protein are attached to the four detection parts in the microfluidic channel 10. The four outlets 5 are connected to the microfluidic channel 10 to externally discharge air and liquid that have been used in the four detection parts.

The sample and control detection parts may be manufactured to have the same volume so that equal volumes of a sample and a control can be supplied into the sample and control detection parts, respectively, when an equal pressure is applied to both the sample and control reservoirs. In addition, the length of a portion of the microfluidic channel between the dye inlet 3 of the dye/buffer inlet part and the outlet 5 of the sample detection part may equal to the length of a portion of the microfluidic channel between the dye inlet 3 of the dye/buffer inlet part and the outlet 5 of one of the control detection parts so that equal volumes of a dye and a buffer can flow toward the sample and the control at the same rate when an equal pressure is applied from the compressed-air inlet 6. The length of a portion of the microfluidic channel between the buffer inlet port of the dye/buffer inlet part and the outlet of the sample detection part may be equal to the length of a portion of the microfluidic channel between the dye inlet of the dye/buffer inlet part and the outlet of one of the control detection parts.

The microfluidic channel 10 may be formed in a polydimethylsiloxan (PDMS) substrate, a glass substrate, a silicon substrate, etc. The microfluidic channel 10 may have a width of 50–500 $\mu$m and a depth of 10–200 $\mu$m. A substrate with the microfluidic channel 10 is combined with, for example, a glass chip, placed in a cartridge, and sealed using, for example, O-rings.

In addition to the above-described cartridge reservoir part 9 and the cartridge, which accommodates the microfluidic channel 10, the microfluidic system according to the present invention includes a compressed-air storage tank connected to the compressed-air inlets 6 by valves 11*c*, a buffer storage tank connected to the buffer inlet ports 4 by valves 11*b*, and a reader that measures the degrees of antigen-antibody reactions in the sample and control detection parts based on variations in dye color.

Compressed air and a buffer are stored in the compressed-air storage tank and the buffer storage tank, respectively. The compressed air and the buffer are forced to flow into the cartridge by a pump 12 that is connected commonly to the compressed-air storage tank and the buffer storage tank.

The reader used in the microfluidic system according to the present invention includes a photodetector that measures color variation data for the sample and the control reacted in the microfluidic channel 10. Any common photodetector that is widely used in the field may be used provided that it can detect a fluorescent signal, a chemiluminescent signal, a phosphorescent signal, etc.

The microfluidic system according to the present invention includes fluid ports as fluid exchange paths between the cartridge and each of the compressed-air storage tank, the buffer storage tank, and other external devices. The fluid ports include the compressed-air inlet ports 6 that are located on the tops of the reservoirs of the cartridge reservoir part 9, respectively, and allow compressed air blown from the compressed-air storage tank to pass, the buffer inlet port 4 connected to the microfluidic channel 10 and through which a buffer is supplied, and the outlets 5 connected to the microfluidic channel 10 and through which used gas and liquid are externally discharged from the microfluidic channel 10.

Flows of fluid through the compressed-air inlet ports 6, the buffer inlet port 4, and the outlets 5 are controlled by the valves 11*a*, 11*b*, and 11*c* that are operated by an automated control system, such as a computer. The valves 11*a*, 11*b*, and 11*c* may be controlled by means of a computer program, such as LabView™. Each of the fluid ports is connected to one of the valves 11*a*, 11*b*, and 11*c* according to their function.

Valves which are connected to the compressed-air inlet ports 6 are three-way valves that are closed to allow external air to flow into the compressed-air inlet ports 6 and are opened toward a pump 12 so that compressed air enters the compressed-air inlet ports 6.

A valve which is connected to the buffer inlet port 4 is a two-way valve that is closed to block a buffer in the buffer storage tank from entering the microfluidic channel 10 and is opened to allow the buffer to enter the microfluidic channel 10.

Valves which are connected to the outlets 5 are two-way valves that are opened to externally discharge gas and liquid used in the microfluidic channel 10.

Figure 3:
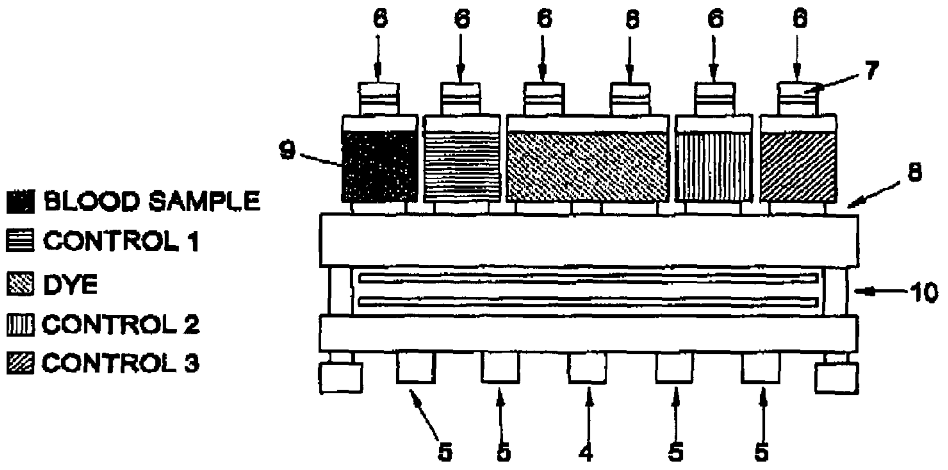
FIG. 3 is an illustration of a cartridge according to the present invention.

A cartridge according to an embodiment of the present invention that includes the cartridge reservoir part 9, the microfluidic channel 10, the compressed-air inlets 6, the buffer inlet port 4, and the outlets 5, is schematically illustrated in FIG. 3. The cartridge is designed to be detachable from the automated fluidic system according to the present invention for easy measurement of color variation data for samples in the cartridge and for easy exchange, repair, and maintenance of the cartridge.

Figure 4:
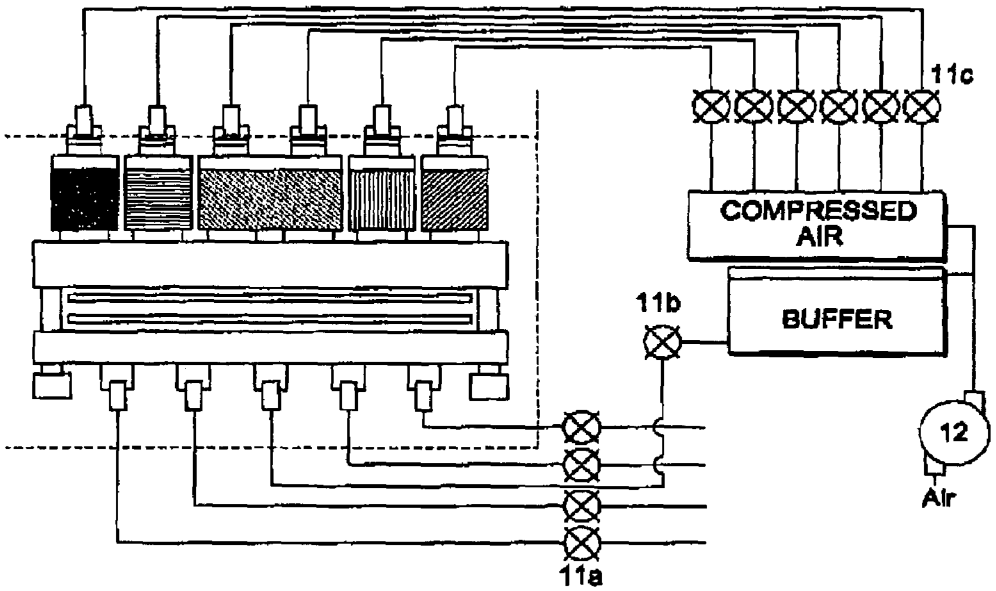
FIG. 4 is an illustration of an automated fluidic system according to the present invention, which includes the cartridge of FIG. 3, a compressed air storage tank, a buffer storage tank, and a detection unit.

FIG. 4 is a schematic view of an automated microfluidic system according to an embodiment of the present invention, which includes the cartridge, the compressed-air storage tank, the buffer storage tank, and the reader.

In an embodiment according to the present invention, when detecting a target protein in a sample using the automated microfluidic system according to the present invention, the antigen-antibody reaction may be induced by supplying compressed air through the compressed-air inlet ports to move the sample in the sample reservoir and the control in the control reservoir into the sample and control detection parts, respectively.

Supplying compressed air is initiated by turning on a switch of the pump 12 connected to the compressed-air storage tank. The pump 12 applies a predetermined pressure to the compressed-air storage tank and the buffer storage tank. In this state where all the valves 11*a*, 11*b*, and 11*c* are not opened yet, the cartridge is not affected by the pressure. However, as valves 11*c* which are connected to the sample and control reservoirs are opened by an automated valve control system, the sample and the control flow along the microfluidic channel 10 and reach the sample and control detection parts, respectively, so that antigen-antibody reactions between the antibodies attached to the internal surface of the microfluidic channel and antigens (target protein) of the sample and the control take place.

When the sample and the control are fully discharged from the sample and control reservoirs, respectively, the valves 11*c* that are connected between the compressed-air inlet ports 6 and the sample and control reservoirs are closed by the valve control system, the valves 11*a* and 11*b* that are connected to the buffer inlet port 4 and the outlets 5 are opened so that the buffer flows into and fills the microfluidic channel 10 connected to the buffer inlet port 4. Once the microfluidic channel 10 has been fully filled with the buffer, the buffer fills the cartridge reservoir part 9 up to the upper hydrophobic barrier 7. As such, the sample and control reservoirs as well as the sample and control detection parts are filled and washed with the buffer.

After washing, the valve 11*b* connected to the buffer inlet port 4 is closed, and the valves 11*c* that are connected between the compressed-air inlet ports 6 and the dye reservoir are opened so that the dye in the dye storage reservoir flows into the microfluidic channel 10 through the dye inlets 3 of the dye/buffer inlet part. The distances between the dye inlets 3 and the outlets 5 of the sample and control detection parts are the same so that equal amounts of a dye flows along the microfluidic channel 10 into the sample and control detection parts to which the antibodies 13 are attached.

After the dye solution is fully discharged, the valves 11*c* connected between the dye reservoir and the compressed-air inlet ports 6 are closed, and the valve 11*b* connected to the buffer inlet port 4 is opened to allow the buffer to flow along the entire microfluidic channel 10 and wash off the dye remaining in the sample and control detection parts.

Finally, after washing the cartridge, color variation data for the sample and control reacted in the sample and control detection parts, respectively, of the cartridge are read by a photodetector. It can be determined whether a particular protein is present in the sample based on the read color variation data. The concentration of the particular protein in the sample can be calculated using a calibration curve of the control.

As described above, an automated microfluidic system according to the present invention that detects a particular protein in a biological sample by ELISA can automate a series of assaying processes, beginning with sample injection and ending with detection, with a simple structure, thereby allowing for convenient and quick detection of a particular protein in a biological sample without requiring skillful, elaborate manipulations by an operator.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An automated microfluidic system that detects a protein in a biological sample, the system comprising:

a cartridge reservoir part including:

a plurality of compressed-air inlets;

a sample reservoir;

a dye reservoir; and a plurality of control reservoirs that contain control solutions of protein of interest;

wherein each of sample reservoir, the dye reservoir, and the control reservoirs has a hydrophobic upper barrier connected to a corresponding one of the compressed-air inlets and a hydrophobic lower barrier connected to a separate liquid outlet;

a cartridge with a microfluidic channel, the cartridge with a microfluidic channel including:

a sample detection part;

a plurality of control detection parts; and a dye/buffer inlet part connected to the sample detection part and control detection parts, wherein each of the sample detection part and the control detection parts has an inlet, an outlet, and an antibody immobilized on an inner surface, the inlets of the sample detection part and the control detection parts being connected to the liquid outlets of the sample reservoir and control reservoirs, respectively; and wherein the dye/buffer inlet part has a dye inlet and a buffer inlet port, the dye inlet being connected to a liquid outlet of the dye reservoir, and both the dye inlet and buffer inlet port being connected to the inlets of the sample detection part and the control detection parts;

a compressed-air storage tank connected to the compressed-air inlet by valves;

a buffer storage tank connected to the buffer inlet ports of the dye/buffer inlet part by a valve; and a reader that measures the degrees of antigen-antibody reactions in the sample and control detection parts based on variations in dye color.

2. The automated microfluidic system of claim 1, wherein the upper hydrophobic barrier and the lower hydrophobic barrier allow only air to pass, not liquid, in an atmospheric pressure.

3. The automated microfluidic system of claim 1, wherein the upper hydropbobic barrier and the lower hydrophobic barrier are porous, and the lower hydrophobic barrier has a larger average pore size than the upper hydrophobic barrier.

4. The automated microfluidic system of claim 3, wherein the upper hydrophobic barrier has an average pore diameter that ranges from 0.2 $\mu$m to 1 $\mu$m, and the lower hydrophobic barrier has an average pore diameter that ranges from 2 $\mu$m to 20 $\mu$m.

5. The automated microfluidic system of claim 1, wherein the upper hydrophobic barrier and the lower hydrophobic barrier are made of porous polytetrafluoro ethylene membranes.

6. The automated microfluidic system of claim 1, further comprising a pump connected to both the compressed-air storage tank and the buffer storage tank.

7. The automated microfluidic system of claim 1, wherein the sample detection part and the control detection parts have the same volume.

8. The automated microfluidic system of claim 1, wherein the length of a portion of the microfluidic channel between the dye inlet of the dye/buffer inlet part and the outlet of the sample detection part is equal to the length of a portion of the microfluidic channel between the dye inlet of the dye/buffer inlet part and the outlet of one of the control detection parts.

9. The automated microfluidic system of claim 1, wherein the length of a portion of the microfluidic channel between the buffer inlet port of the dye/buffer inlet part and the outlet of the sample detection part is equal to the length of a portion of the microfluidic channel between the dye inlet of the dye/buffer inlet part and the outlet of one of the control detection parts.

10. The automated microfluidic system of claim 1, wherein the valves that connect the compressed-air inlets and the compressed-air storage tank are closed when a compressed air is supplied into the compressed-air storage tank, opened when a sample and the control solutions flow into the sample reservoir and the control reservoirs, respectively, and further closed when the sample and the control solutions are discharged from the sample and control reservoirs.

11. The automated microfluidic system of claim 1, further comprising a controller that controls the opening and closing of the outlets of the sample detection part and the control detection parts.

12. The automated microfluidic system of claim 1, wherein the hydrophobic upper barrier passes a predetermined liquid only when a pressure applied to the hydrophobic upper barrier is higher than a pressure applied to the hydrophobic lower barrier.

* * * * *